(12) United States Patent
Hafizovic et al.

(10) Patent No.: US 9,114,348 B2
(45) Date of Patent: Aug. 25, 2015

(54) METAL ORGANIC FRAMEWORK COMPOUNDS

(71) Applicant: Universitetet i Oslo, Oslo (NO)

(72) Inventors: Jasmina Hafizovic, Oslo (NO); Unni Olsbye, Oslo (NO); Karl Petter Lillerud, Oslo (NO); Soren Jakobsen, Oslo (NO); Nathalie Guillou, Oslo (NO)

(73) Assignee: UNIVERSITETET I OSLO, Blindern (NO)

( * ) Notice: Subject to any disclaimer, the term of this patent is extended or adjusted under 35 U.S.C. 154(b) by 0 days.

(21) Appl. No.: 14/144,450

(22) Filed: Dec. 30, 2013

(65) Prior Publication Data

US 2014/0322123 A1 Oct. 30, 2014

Related U.S. Application Data

(62) Division of application No. 12/989,641, filed as application No. PCT/GB2009/001087 on Apr. 29, 2009, now Pat. No. 8,653,292.

(30) Foreign Application Priority Data

Apr. 29, 2008 (GB) .................... 0807862.8

(51) Int. Cl.
*C07F 7/00* (2006.01)
*B01J 31/00* (2006.01)
(Continued)

(52) U.S. Cl.
CPC ............. *B01D 53/02* (2013.01); *B01J 31/1691* (2013.01); *C01B 3/56* (2013.01); *C01B 21/0455* (2013.01); *C01B 31/20* (2013.01); *C07C 7/12* (2013.01); *C07C 63/14* (2013.01); *C07C 63/15* (2013.01); *C07C 63/307* (2013.01); *C07F 7/006* (2013.01); *B01D 2253/204* (2013.01); *B01J 2531/48* (2013.01)

(58) Field of Classification Search
CPC B01D 2253/204; C01B 3/56; C01B 21/0455; C01B 31/20; C07C 7/12; C07F 7/006
USPC .............................. 556/55; 502/171; 428/219
See application file for complete search history.

(56) References Cited

U.S. PATENT DOCUMENTS

2004/0081611 A1 4/2004 Muller et al.
2004/0225134 A1 11/2004 Yaghi et al.
(Continued)

FOREIGN PATENT DOCUMENTS

WO 20040101575 A2 11/2004
WO 2007118874 A1 10/2007
(Continued)

OTHER PUBLICATIONS

J. H. Cavka, S. Jakobsen et al., "A New Zirconium Inorganic Building Brick Forming Metal Organic Frameworks with Exceptional Stability", J. Am. Chem. Soc., vol. 130, No. 42, pp. 13850-13851, (2008).
(Continued)

*Primary Examiner* — Porfirio Nazario Gonzalez
(74) *Attorney, Agent, or Firm* — IPHORGAN LTD.

(57) ABSTRACT

The invention provides novel Zr MOFs, in particular compounds having a surface area of at least 1020 $m^2/g$ or if functionalized, having a surface area of at least 500 $m^2/g$.

9 Claims, 5 Drawing Sheets

(51) Int. Cl.
  *C01B 3/56* (2006.01)
  *B01D 53/02* (2006.01)
  *B01J 31/16* (2006.01)
  *C07C 63/14* (2006.01)
  *C07C 63/15* (2006.01)
  *C07C 63/307* (2006.01)
  *C01B 21/04* (2006.01)
  *C01B 31/20* (2006.01)
  *C07C 7/12* (2006.01)

(56) References Cited

U.S. PATENT DOCUMENTS

2007/0068389 A1    3/2007   Yaghi
2007/0227898 A1   10/2007   Muller et al.
2009/0198079 A1*   8/2009   Schubert et al. ............... 556/55

FOREIGN PATENT DOCUMENTS

WO    WO 2007/118888 A1 * 10/2007
WO       20080000694 A2     1/2008

OTHER PUBLICATIONS

H. L. Ngo et al., "Molecular Building Block Approaches to chiral porous zirconium phosphonates for asymmetric catalysis", J. Molecular Catalysis, vol. 215, No. 1-2, pp. 177-186, (2004).
A. Hu et al., "Chiral porous hybrid solids for practical heterogeneous asymmetric hydrogentation of aromatic ketones", J. Am. Chem. Soc., vol. 125, 2003, pp. 11490-11491.
K. Sanderson, "Space Invaders", Nature, 2007, pp. 746-748.
International Search Report and Written Opinion, PCT/GB2009/001087, European Patent Office acting as the International Search Authority, Nov. 17, 2009.

* cited by examiner

METAL ORGANIC FRAMEWORK COMPOUNDS

This application is a continuing application of U.S. application Ser. No. 12/989,641, filed Oct. 25, 2010, which is the national stage completion application of PCT Application Number PCT/GB2009/001087, filed Apr. 29, 2009, which claims priority from Application Number GB 0807862.8, filed Apr. 29, 2008. Each of these applications is incorporated by reference herein in its entirety.

This invention relates to Zr-MOFs, to their production, to their use, and to compositions and devices containing them.

MOFs or "metal organic frameworks" are compounds having a lattice structure having vertices or "cornerstones" which are metal-based inorganic groups, for example metal oxides, linked together by organic linker groups. These compounds have been developed by, for example, Omar Yaghi and co-workers, currently of the University of Michigan, and are promising materials for many applications.

Thus for example MOFs have been proposed for gas storage, as catalyst materials and so on.

Perhaps the best known MOF is MOF-5 in which each $Zn_4O$ cornerstone is coordinated by six bis-carboxylate organic linkers.

Other MOFs in which the inorganic cornerstone is for example chromium, copper, vanadium, cadmium and iron have been made.

The utility of the known MOFs however is limited by their thermal and chemical sensitivity.

WO 2007/118874 discloses Zr-MOFs wherein the organic linkers are terephthalic acid. The Zr-MOFs taught in this document however possess a surface area of at most 836 $m^2/g$.

We have now surprisingly found that Zr-MOFs with excellent stability, porosity and surface areas may be made using cornerstones based on Zr.

Thus viewed from one aspect the invention provides a Zr-MOF having a surface area of at least 1020 $m^2/g$, especially at least 1050 $m^2/g$, particularly at least 1200 $m^2/g$, for example up to 10000 $m^2/g$, especially up to 5000 $m^2/g$.

The Zr-MOFs of the invention particularly preferably have a cornerstone having at least 20 coordination sites for the organic linkers, e.g. 20-36, especially preferably at least 24, 30 or 36, most especially 24. In this way at least 10, more preferably at least 12 bidentate ligand groups of the organic linkers can bind to each cornerstone. Previously the highest known number of coordination sites has been 18 for a Cr-MOF (the zinc-based MOF-5 has 12 coordination sites).

Especially preferably the cornerstone is a $Zr_6O_{32}$ structure, which has 24 coordination sites per cornerstone.

Thus viewed from a further aspect the invention provides a Zr-MOF the inorganic cornerstones of which have at least 20 coordination sites, and preferably having a surface area of at least 1020 $m^2/g$, especially at least 1050 $m^2/g$, particularly at least 1200 $m^2/g$, for example up to 5000 $m^2/g$, etc as above.

Viewed from a still further aspect the invention provides a Zr-MOF comprising $Zr_6O_{32}$ cornerstones, and preferably having a surface area of at least 1020 $m^2/g$, etc as above.

Viewed from another aspect the invention provides a Zr-MOF having a Zr metal atom to organic linker molecule ratio of from 1:0.45 to 1:0.55, especially 1:0.49 to 1:0.51, particularly 1:0.5, and preferably having a surface area of at least 1020 $m^2/g$, etc as above.

Other preferred Zr metal atom to organic linker molecule ratios are about 0.5:1, about 1:1, about 3:1 and about 1:3.

One especial advantage of such high numbers of coordination sites is that functionalisation of the organic linkers may be effected, e.g. to carry catalytic sites, without seriously weakening the MOF structure.

Viewed from another aspect the invention provides a functionalised Zr-MOF having a surface area of at least 500 $m^2/g$, especially at least 600 $m^2/g$, especially at least 700 $m^2/g$, particularly at least 1020 $m^2/g$ etc as described above for unfunctionalised Zr-MOFs.

By functionalised MOF is meant a MOF, wherein one or more of the backbone atoms of the organic linkers thereof carries a pendant functional group or itself forms a functional group. Functional groups are typically groups capable of reacting with compounds entering the MOF or acting as catalytic sites for reaction of compounds entering the MOF. Suitable functional groups will be apparent to a person skilled in the art and in preferred embodiments of the invention include amino, thiol, oxyacid, halo and cyano groups or heterocyclic groups (e.g. pyridine), each optionally linked by a linker group, e.g. $C_{1-6}$, preferably carbonyl. The functional group may also be a phosphorus- or sulfur-containing acid.

If an acid functional group possesses more than one labile hydrogen, then one or more of said labile hydrogens may itself be substituted leaving one labile hydrogen.

If desired, a precursor to the functional group can be prepared, for example an ether or ester group, or their phosphorous or sulfur equivalents.

The functionalised or unfunctionalised MOFs of the invention will preferably have the cornerstones and/or Zr metal atom to organic linker molecule ratios referred to above.

The new Zr-MOFs of the invention, besides having very high surface areas, and thus the ability to adsorb large volumes of gas, have both high thermal and chemical stability, especially water stability. Moreover because of the nature of Group 4 metals, the Zr metal can be in more than one oxidation state. This makes the Zr-MOFs of the invention ideal candidates for use as catalysts (e.g. in olefin polymerization), or more especially as electrodes in lithium batteries. The chemical stability, in particular stability to exposure to water, a property rare in conventional MoFs, extends the range of possible applications, e.g. to include use in sustained release pharmaceutical formulations. The thermal stability makes the Zr-MOFs of the invention particularly suited for gas storage since gas release is generally effected by raising the temperature of the MOF.

We have also surprisingly found that Zr produces MOFs in which the structure is porous and three-dimensional and does not comprise two or more interpenetrating MOF structures, and so as a result the pore volume is large and the structure open. This makes these MOFs particularly suitable for most applications.

In conventional lithium batteries, e.g. lithium ion or lithium polymer batteries, a graphite electrode is used. Repeated charging of the batteries results in collapse of the graphite and as a consequence in shorter battery life. The Zr-MOFs of the invention have a strong and stable 3D structure and a wide range of possible oxidation states for Zr making them especially suitable for use in place of graphite as the electrode material.

Thus viewed from a further aspect the invention provides the use of a Zr-MOF as an electrode material in a lithium battery. Viewed from a further aspect the invention provides a lithium battery having therein a Zr-MOF as electrode material.

The lithium batteries according to the invention may produced simply by substituting the Zr-MOF for the graphite in a conventional lithium battery.

The Zr-MOFs of the invention are also particularly suitable for containing gases due to their very high surface area and stability. The types of gases of interest are principally fuel gases such as hydrogen, methane and acetylene; however other gases may be adsorbed and, under raised temperature or reduced pressure, desorbed—thus they can also be used to capture gaseous contaminants or to hold other gases such as for example nitrogen, carbon monoxide or carbon dioxide. Accordingly, viewed from a further aspect, the invention provides the use of a Zr-MOF to retain a gas, preferably hydrogen, methane or acetylene. Viewed from a further aspect the invention provides a gas container, e.g. a fuel tank for a motor vehicle, comprising a sealable vessel containing a Zr-MOF, optionally containing a gas, preferably hydrogen, methane or acetylene. Viewed from a further aspect the invention provides a hydrogen fuel cell having a hydrogen reservoir containing a Zr-MOF. Once again such devices may be constructed in conventional fashion.

Unlike most MOFs, we have found Zr-MOFs to be water- and acid-stable. They can therefore be used as drug reservoirs for pharmaceuticals for administration into the gastrointestinal tract or for depot placement subcutaneously whereby to achieve a sustained release of the drug. Sustained release allows the effect of the drug to continue longer and so allows less fragment administration. Thus viewed from a further aspect the invention provides physiologically tolerable Zr-MOFs for use in medicine. Viewed from another aspect the invention provides the use of a physiologically tolerable Zr-MOF for the manufacture of a sustained release medicament for use in a method of treatment of a human or non-human animal. Viewed from another aspect the invention provides a sustained release pharmaceutical composition comprising a physiologically tolerable Zr-MOF containing a drug substance, e.g. a substance with therapeutic or prophylactic effect or with utility in diagnosis. Viewed from a still further aspect the invention provides a method of treatment of a human or non-human animal subject which comprises administering an effective amount of a drug substance to said subject, the improvement comprising administering said substance contained at least in part within a physiologically tolerable Zr-MOF. Administration will generally be oral, rectal, vaginal or via subcutaneous depot placement, preferably oral. The drug substance may be any drug substance for which sustained release is desirable, e.g. an anti-infective, anti-inflammatory or anticancer agent, etc. Uptake of the drug substance by the MOF will generally be by contacting the MOF with a solution, e.g. an aqueous solution, of the drug substance.

Biodegradation of the MOF will either not occur with the MOF being excreted intact or will generally release the organic linkers and the inorganic cornerstones. The cornerstones will generally be excreted intact and physiologically tolerable organic linkers may be selected with ease for MOF production. The drug loaded MOFs may be tabletted, encapsulated, put into dispersion or otherwise simply formulated into the dosage forms for administration using conventional pharmaceutical techniques.

The Zr-MOFs may also be used as catalysts, either relying on the catalytic activity of Zr, by using linkers with catalytic activity or by loading the MOF with a catalyst, e.g. a material which is simply absorbed into the MOF or which will bind to free functionalities on the organic linkers in the MOF. Catalyst loading and subsequent reagent loading may be performed in conventional fashion. Thus viewed from a further aspect the invention provides a catalyzed process for reacting a reagent to produce a product, characterized in that as the catalyst or catalyst carrier is used a Zr-MOF. Viewed from another aspect the invention provides the use of a Zr-MOF as a catalyst or catalyst support. Viewed from a still further aspect the invention provides a Zr-MOF material having catalytic activity. Performance of catalyzed reactions within porous structures is known to allow great reaction specificity and the Zr-MOFs may advantageously be used to this end.

The organic linkers of the Zr-MOFs of the invention may be any linker molecule or molecule combination capable of binding to at least two inorganic cornerstones and comprising an organic moiety. Thus the linker may be any of the linkers conventionally used in MOF production (see for example the publications by Omar Yaghi et al). These are generally compounds with at least two cornerstone binding groups, e.g. carboxylates, optionally with extra functional groups which do not bind the cornerstones but may bind metal ions on other materials it is desired to load into the MOF. The introduction of such extra functionalities is straightforward as is described for example by Campbell in JACS 82:3126-3128 (1960). The linkers moreover typically have rigidifying groups between the cornerstone-binding groups to facilitate 3D MOF formation. Examples of suitable organic linker compounds include oxalic acid, ethyloxalic acid, fumaric acid, 1,3,5-benzene tribenzoic acid (BTB), DCPB, benzene tribiphenylcarboxylic acid (BBC), 5,15-bis(4-carboxyphenyl) zinc (II) porphyrin (BCPP), 1,4-benzene dicarboxylic acid (BDC), 2-amino-1,4-benzene dicarboxylic acid ($R_3$-BDC or $H_2N$ BDC), 1,1'-azo-diphenyl 4,4'-dicarboxylic acid, cyclobutyl-1,4-benzene dicarboxylic acid ($R_6$-BDC), benzene tricarboxylic acid, 2,6-naphthalene dicarboxylic acid (NDC), 1,1'-biphenyl 4,4'-dicarboxylic acid (BPDC), 2,2'-bipyridyl-5,5'-dicarboxylic acid, adamantane tetracarboxylic acid (ATC), adamantane dibenzoic acid (ADB), adamantane teracarboxylic acid (ATC), dihydroxyterephthalic acid (DHBDC), biphenyltetracarboxylic acid (BPTC), tetrahydropyrene 2,7-dicarboxylic acid (HPDC), hihydroxyterephthalic acid (DHBC), pyrene 2,7-dicarboxylic acid (PDC), pyrazine dicarboxylic acid, acetylene dicarboxylic acid (ADC), camphor dicarboxylic acid, fumaric acid, benzene tetracarboxylic acid, 1,4-bis(4-carboxyphenyl)butadiyne, nicotinic acid, and terphenyl dicarboxylic acid (TPDC). Other acids besides carboxylic acids, e.g. boronic acids may also be used. A mixture of linkers may be used to introduce functional groups within the pore space, e.g. by using aminobenzoic acid to provide free amine groups or by using a shorter linker such as oxalic acid. This introduction of functionalised linkers is facilitated since the Zr-MOFs have excess inorganic cornerstone coordination sites beyond those required to form the stable 3D MOF structure.

MOF construction is effected in solution, typically an organic solvent, for example DMF, using a soluble precursor Zr compound and the organic linker and preferably in a molar ratio of from 0.6:1 to 3:1, particularly 0.8:1 to 2:1 especially about 1:1. The solution is generally heated, for example to 60 to 150° C., preferably 100 to 140° C., especially 110 to 130° C., particularly 115 to 125° C. (e.g. 80 to 130° C. or 100 to 120° C.), and MOF formation is preferably allowed to occur under static conditions, e.g. for up to 96 hours, especially 12 to 72 hours, particularly 24 to 48 hours, (e.g. for 10 to 30 hours, especially 15 to 19 hours). The use of too long a formation period, e.g. 7 days, or too high a formation temperature (e.g. at or above the upper limits mentioned above) is generally undesirable as the surface area of the resulting MOF tends to be reduced. The Zr is preferably present in the reaction solution at a concentration of 0.3-2.0 M, especially 0.5-1.0 M, particularly 0.6-0.8 M. The reaction is preferably effected under an oxygen-free atmosphere and using water-free solvents. The resulting MOF should then be washed with solvent (conveniently the one used for the MOF formation reaction) and thoroughly dried. The surface area can be determined by use of nitrogen adsorption and the BET method. This method, by which the surface areas referred to herein may be determined, is described by Rouquerol et al in "Adsorption by powders and porous solids", Academic Press, San Diego, Calif., USA, 1999.

The solvent used is conveniently an alkanol, dimethyl formamide (DMF), toluene, methylethyl ketone, dimethylsulphoxide, tetrahydrofuran, cyclohexanone, diethyl formamide, N-methylpyrridone, acetone, an alkane, pyridine or acetonitrile. The use of DMF is especially preferred.

The Zr compound used is preferably a halide (e.g. the chloride), an alcoholate or an acetonate. The metal may if desired be present in such a reagent as an oxide cation.

The MOFs used as an electrode material in a lithium battery, or to retain a gas, or for use in a hydrogen fuel cell, or for use in medicine, or used for the manufacture of a sustained release medicament, or for use as a catalyst carrier, catalyst support or catalyst, or having catalytic activity are preferably MOFs of the invention.

The invention will now be described further with reference to the following non-limiting Examples and the accompanying drawings, in which.

EXAMPLE 1

Zr-BDC MOF

Standard synthesis of Zr-BDC MOF was performed by dissolving $ZrCl_4$ (0.053 g, 0.227 mmol, Aldrich) and 1,4-benzenedicarboxylic acid ($H_2BDC$) (0.034 g, 0.227 mmol, Aldrich) in N,N'-dimethylformamide (DMF) (24.9 g, 340 mmol) at ambient temperature. The thus obtained mixture was sealed and placed in a pre-heated oven at 120° C. for 24 hours. Crystallization was carried out under static conditions. After cooling in air to ambient temperature the resulting solid was filtered, repeatedly washed with DMF and dried at ambient temperature.

EXAMPLE 2

Zr-BPDC MOF

Standard synthesis of Zr-BPDC MOF was performed by dissolving $ZrCl_4$ (0.0528 g, 0.230 mmol, Aldrich) and biphenyl-4,4-dicarboxylic acid ($H_2BPDC$) (0.055 g, 0.230 mmol, Aldrich) in N,N'-dimethylformamide (DMF) (24.9 g, 340 mmol) at ambient temperature. The thus obtained mixture was sealed and placed in a pre-heated oven at 120° C. for 24 hours. Crystallization was carried out under static conditions. After cooling in air to ambient temperature the resulting solid was filtered, repeatedly washed with DMF and dried at ambient temperature. The surface area is estimated to be in the region of 1800 $m^2/g$.

EXAMPLE 3

Zr-TPDC MOF

Standard synthesis of Zr-TPDC MOF was performed by dissolving $ZrCl_4$ (0.0528 g, 0.230 mmol, Aldrich) and terphenyl dicarboxylic acid ($H_2TPDC$) (0.072 g, 0.230 mmol, Aldrich) in N,N'-dimethylformamide (DMF) (24.9 g, 340 mmol) at ambient temperature. The thus obtained mixture was sealed and placed in a pre-heated oven at 120° C. for 24 hours. Crystallization was carried out under static conditions. After cooling in air to ambient temperature the resulting solid was filtered, repeatedly washed with DMF and dried at ambient temperature. The surface area is estimated to be in the region of 4000 $m^2/g$.

EXAMPLE 4

Powder X-Ray Diffraction Patterns

Powder XRD patterns of the Zr-MOFs of Examples 1 to were obtained with Siemens Bruker AXS D-5000 instruments using CuK-alpha-1 radiation in Bragg-Brentano reflecting and Debye-Scherrer transmission geometry. The samples were thoroughly ground and transferred into 0.5 mm quartz capillaries or deposited on glass plates. Powder patterns of desolvated samples were recorded after heating the samples to 300° C. for 60 minutes, and sealing the capillaries before cooling to ambient temperature. The patterns for the desolvated samples were used to solve the crystal structures.

A temperature resolved series of powder XRD patterns was recorded with a Siemens D500 diffractometer using Cu radiation. The instrument was equipped with beta-filter and Scintillator counter. Powder XRD patterns were collected in the temperature range 25-450° C. in steps of 25° C. and in nitrogen flow.

Figure 1:
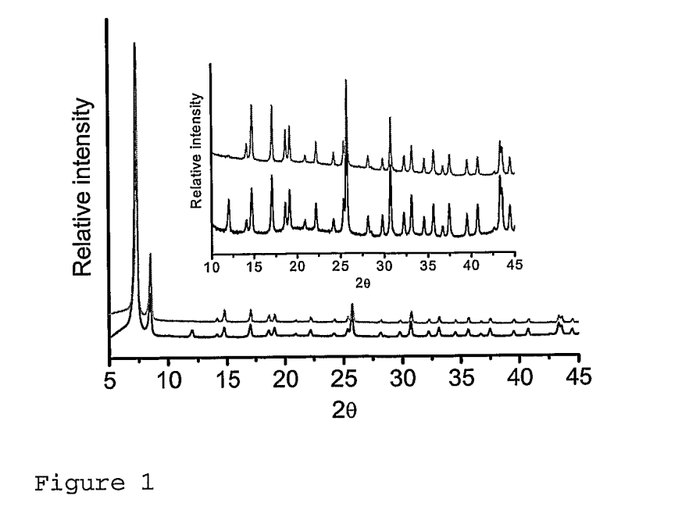
FIG. 1 shows CuKα1 powder X-ray diffraction patterns of Zr-BDC MOF.
Figure 4:
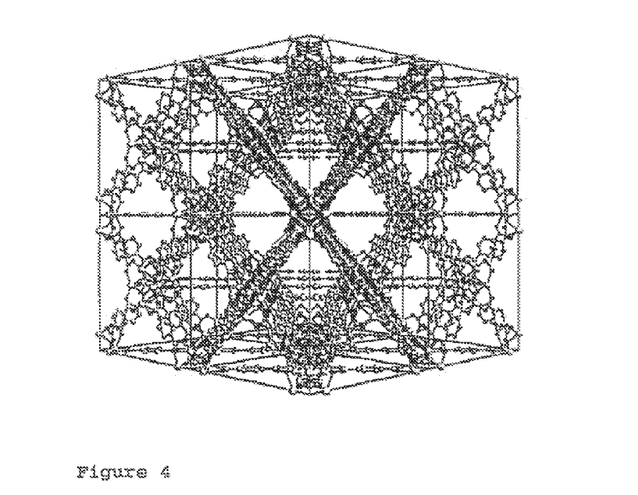
FIG. 4 is a representation of the structure of Zr-BDC MOF.

The powder X-ray diffraction patterns for as-synthesised and desolvated Zr-BDC MOF (Example 1) are shown in FIG. 1. The upper trace is the desolvated Zr-BDC MOF, the lower the Zr-BDC MOF as synthesised. A representation of the structure calculated for Zr-BDC MOF is shown in FIG. 4.

Figure 2:
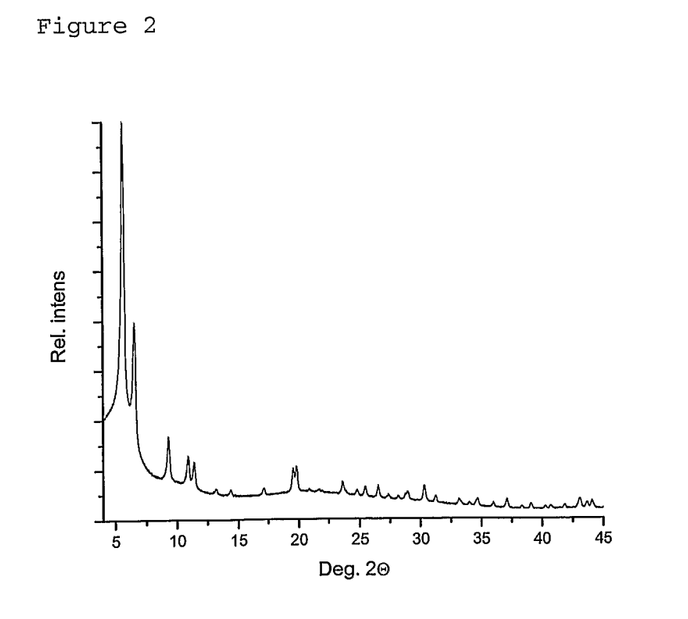
FIG. 2 is a CuKα1 powder X-ray diffraction pattern of Zr-BPDC MOF.
Figure 5:
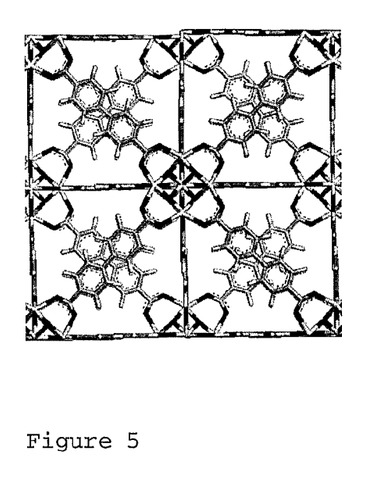
FIG. 5 is a representation of the structure of Zr-BPDC MOF.

The powder X-ray diffraction pattern for as synthesised Zr-BPDC MOF (Example 2) is shown in FIG. 2. A representation of the structure calculated for Zr-BPDC MOF is shown in FIG. 5.

Figure 3:
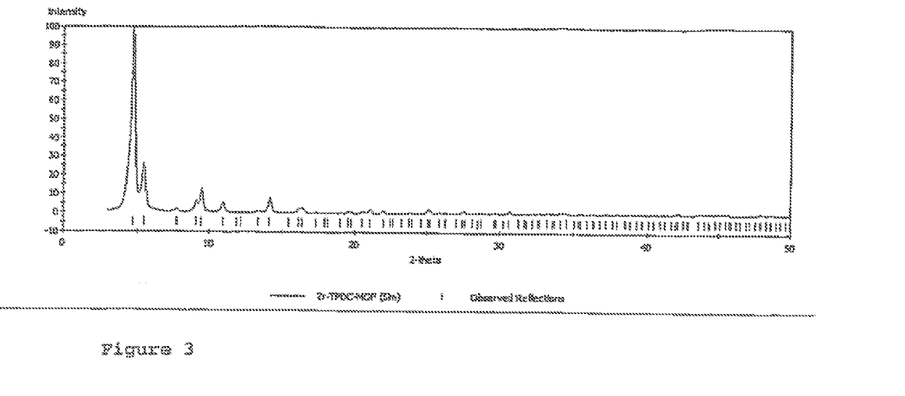
FIG. 3 is a simulated CuKα1 powder X-ray diffraction pattern of Zr-TPDC MOF also showing the observed diffraction peaks on the baseline.
Figure 9:
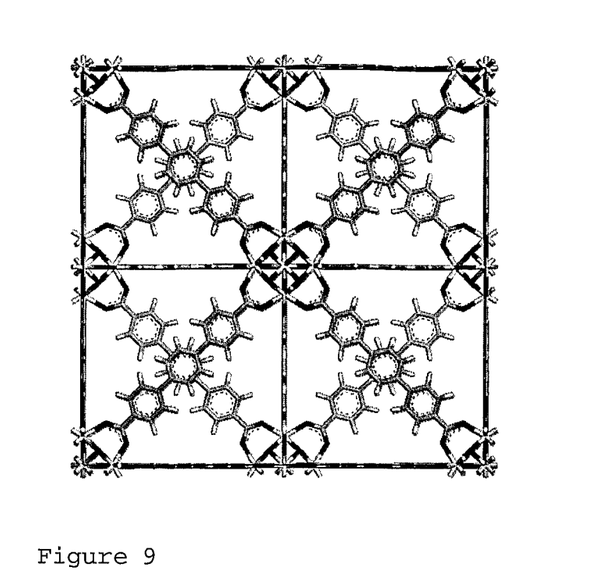
FIG. 9 is a representation of the structure of Zr-TPDC MOF.
Figure 10:
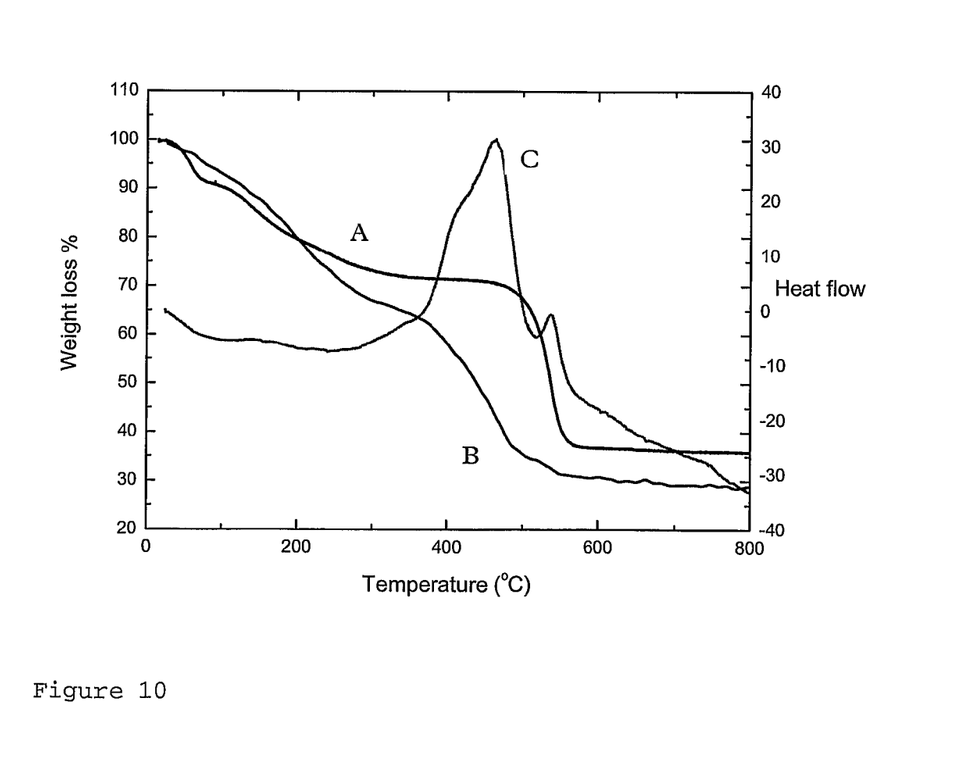
FIG. 10 is a thermogravimetric curve for Zr-BDC MOF-$NH_2$ (B) compared to that of Zr-BDC MOF (A) wherein curve (C) depicts the heat flow.

The simulated powder X-ray diffraction pattern for as synthesised Zr-TPDC MOF (Example 3) is shown in FIG. 3 with the observed peaks shown on the baseline. A representation of the structure calculated for Zr-TPDC MOF is shown in FIG. 9.

EXAMPLE 5

Thermogravimetric Analysis and Temperature Programmed Adsorption/Desorption

Thermogravimetric (TG) analysis and temperature programmed adsorption/desorption (TPA/TPD) were carried out in flowing nitrogen atmosphere (15 mL/min) using a Rheometric Scientific STA 1500 instrument. The TG analyses were performed parallel with on-line mass spectrometric (MS) analysis. The MS data were recorded with Pfeiffer OmniStar GDS 300 O quadrupole equipped with an electron multiplier detector. The approximate sample weight was 10 mg in all experiments and the heating rate in TG experiment was 5 C.°/min. In the TPA/TPD experiments, the solvent molecules in the structure were removed by heating the sample to 300° C. (heating rate 10 C.°/min). The sample was than cooled to 25° C. and carrier gas (nitrogen) saturated with probe molecules (water and DMF) was admitted to the sample. After weight stabilization, the sample was reheated again to 300° C.

The adsorption of nitrogen was measured volumetrically with a BELSORP-mini II instrument and the specific surface area was obtained by the BET method. The sample was heated to 250° C. and kept at this temperature under continuous evacuation for 6 hours prior to adsorption measurement. The hydrogen, methane, and carbon dioxide adsorption isotherms were recorded on an Autosorb Quanta Chrome instrument after pretreating of sample at 250° C. for 1 hour.

Figure 6:
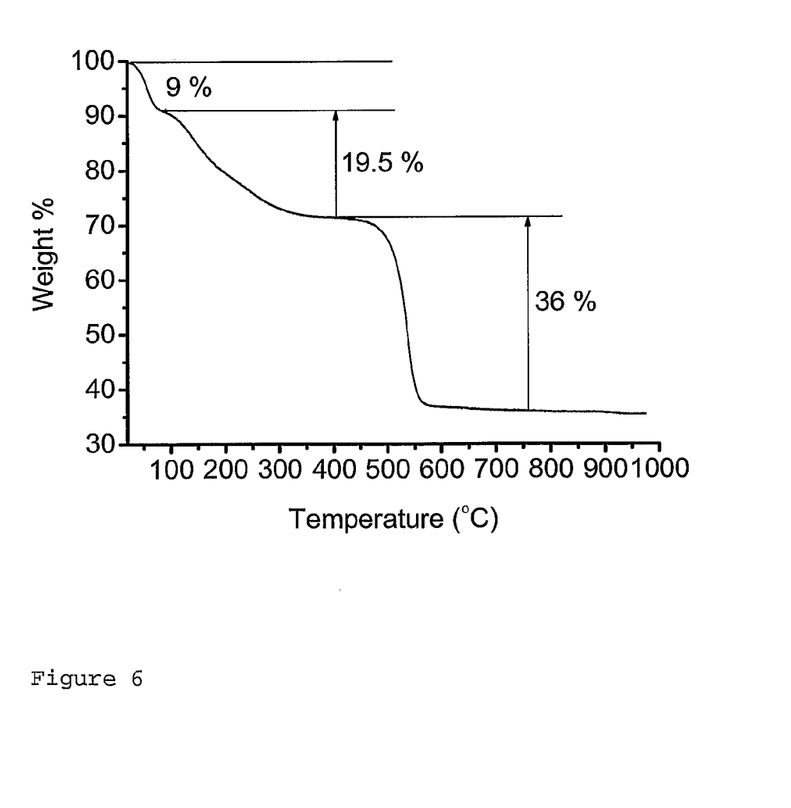
FIG. 6 is a thermogravimetric curve for Zr-BDC MOF.

The thermographic curve recorded for Zr-BDC MOF (Example 1) is shown in FIG. 6. As can be seen, the material is stable up to about 500° C.

Figure 7:
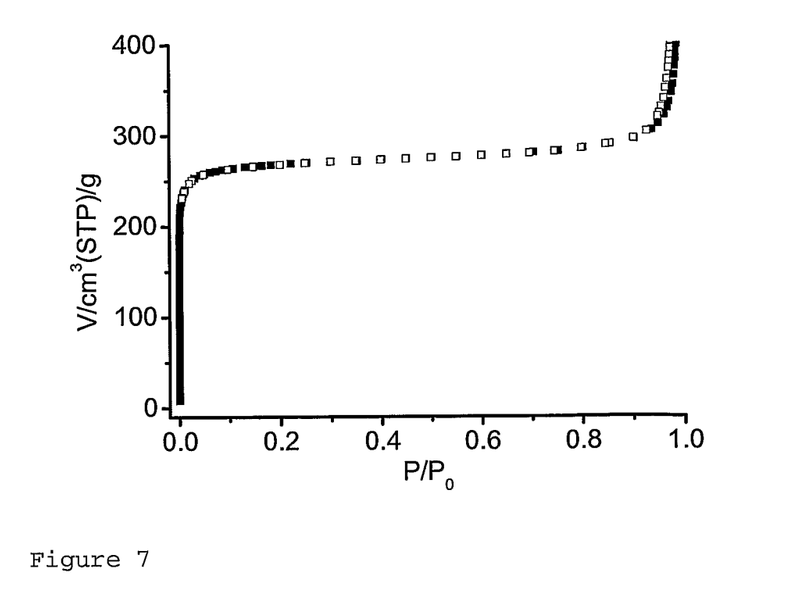
FIG. 7 shows BET nitrogen adsorption and desorption isotherms for Zr-BDC at 77° K.

The recorded nitrogen adsorption/desorption plot for Zr-BDC MOF at 77° K is shown in FIG. 7. Solid squares and open squares are respectively data points for adsorption and desorption. The adsorption of nitrogen follows a type I isotherm with no hysteresis, and with a BET surface area of 1069 $m^2/g$ (corresponding to a Langmuir surface area of 1191.5 $m^2/g$).

Figure 8:
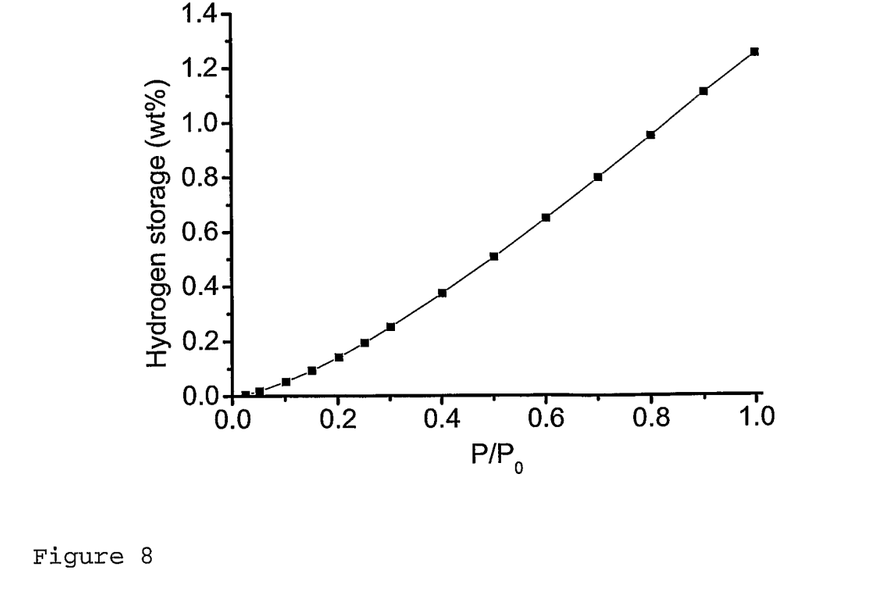
FIG. 8 is the hydrogen adsorption isotherm for Zr-BDC at 77° K.

The recorded hydrogen adsorption isotherm for Zr-BDC MOF at 77° K is shown in FIG. 8. The hydrogen storage capacity is 1.2 wt % at standard temperature and pressure (STP).

EXAMPLE 6

Zr-carborane MOF a) Preparation of 1,12-Dihydroxycarbonyl-1,12-dicarba-closo-dodecaborane 1,12-Dihydroxycarbonyl-1,12-dicarba-closo-dodecaborane was synthesised by the method of Hubbs, i.e. by adding 1.6M (35 mL, 56 mmol) n-BuLi via syringe to 2 g (13.9 mmoles) of 1,12-dicarba-closododecaborane (p-carborane), dissolved in 150 mL of dry diethyl ether and stirred at 0° C. The reaction mixture was warmed to ambient temperature and then refluxed for 1.5 hours. The reaction was then cooled to −78° C. utilizing a dry-ice/acetone bath. Carbon dioxide gas was bubbled into the reaction mixture for an hour while stirring. Diethyl ether was concentrated and the white solid was stirred in 100 mL of 3M hydrochloric acid.

The thus obtained precipitate was filtered and washed in the following order: chilled water, hexane, chloroform. The title product was obtained as white solid (2.81 g, 87%) and dried under vacuum overnight.

b) Preparation of Zr-carborane MOF $ZrCl_4$ (0.027 g, 0.11 mmol, Aldrich), $Zn(NO_3)_2 \cdot 6H_2O$ (33 mg, 0.11 mmol) and 1,12-dicarboxylic-1,12-dicarba-closo-dodecaborane (8.3 mg, 0.035 mmol) were dissolved in a vial in 1 ml of dimethylformamide. The solution was heated at 100° C. for 24 hours to yield the Zr-carborane MOF.

EXAMPLE 7

Zr-BDC MOF-$NH_2$

To further expand the scope of use for the Zr-MOFs we have now incorporated an amine group into the structure by the use of 2-aminoterephthalic acid during synthesis, thereby synthesising the MOF Zr-BDC MOF-$NH_2$ with the same morphology as Zr-BDC MOF.

The solvent interaction is stronger in this functionalized MOF. DMF must be exchanged with ethanol or methanol before evacuation in order to observe a surface area that is close to the calculated value of 900 $m^2/g$.

Standard synthesis of Zr-BDC MOF-$NH_2$ was performed by dissolving $ZrCl_4$ (0.053 g, 0.227 mmol, Aldrich) and 2-aminoterephthalic acid (0.041 g, 0.227 mmol, Aldrich) in N,N'-dimethylformamide (DMF) (24.9 g, 340 mmol) at ambient temperature. The thus obtained mixture was sealed and placed in a pre-heated oven at 120° C. for 24 hours. Crystallization was carried out under static conditions. After cooling in air to ambient temperature the resulting solid was filtered, repeatedly washed with DMF and dried at ambient temperature.

EXAMPLE 8

Zr-bipyridine MOF

Standard synthesis of Zr-dipyridine MOF was performed by dissolving $ZrCl_4$ (0.047 g, 0.22 mmol, Aldrich) and 2,2'-bipyridine-5,5-dicarboxylic acid (0.0488 g, 0.227 mmol, Aldrich) in N,N'-dimethylformamide (DMF) (24.9 g, 340 mmol) at ambient temperature. The thus obtained mixture was sealed and placed in a pre-heated oven at 100° C. for 48 hours. Crystallization was carried out under static conditions. After cooling in air to ambient temperature the resulting solid was filtered, repeatedly washed with DMF and dried at ambient temperature.

EXAMPLE 9

Zr-bipyridine-Pt MOF

Standard synthesis of Zr-dipyridine-Pt MOF was performed by dissolving $ZrCl_4$ (0.047 g, 0.22 mmol, Aldrich) and 2,2'-bipyridine-5,5-dicarboxylic acid (0.0488 g, 0.227 mmol, Aldrich) and $K_2PtCl_6$ (99.6 mg) in N,N'-dimethylformamide (DMF) (24.9 g, 340 mmol) at ambient temperature. The thus obtained mixture was sealed and placed in a pre-heated oven at 100° C. for 48 hours. Crystallization was carried out under static conditions. After cooling in air to ambient temperature the resulting solid was filtered, repeatedly washed with DMF and dried at ambient temperature.

The invention claimed is:

1. A method of storing a gas comprising the step of absorbing said gas onto a Zr-MOF wherein the Zr-MOF has surface area of at least 1020 $m^2/g$.

2. A method of storing a gas comprising the step of absorbing said gas onto a Zr-MOF wherein the Zr-MOF is a Zr-MOF comprising $Zr_6O_{32}$ cornerstones.

3. A method of storing a gas comprising the step of absorbing said gas onto a Zr-MOF wherein the Zr-MOF has the inorganic cornerstones which have at least 20 coordination sites.

4. The method of claim 3 wherein the Zr-MOF is a functionalised Zr-MOF having a surface area of at least 500 $m^2/g$.

5. The method of claim 3 wherein the Zr-MOF has a Zr metal atom to organic linker molecule ratio of from 1:0.45 to 1:0.55.

6. The method of claim 3 wherein said gas is at least one selected from hydrogen, methane, acetylene, nitrogen, carbon monoxide and carbon dioxide.

7. The method of claim 3 wherein said gas is at least one selected from hydrogen, methane and acetylene.

8. The method of claim 3 wherein said Zr-MOF is contained within a sealable vessel.

9. The method of claim 3 wherein said gas is released from storage by raised temperature and/or reduced pressure.

* * * * *